United States Patent [19]

November et al.

[11] 4,037,460
[45] July 26, 1977

[54] DENSITOMETER

[75] Inventors: Milton H. November, Hacienda Heights; LaVerne D. Lyon, Claremont, both of Calif.

[73] Assignee: International Telephone and Telegraph Corporation, New York, N.Y.

[21] Appl. No.: 709,582

[22] Filed: July 29, 1976

[51] Int. Cl.² ............................................. G01N 9/00
[52] U.S. Cl. ................................................. 73/32 A
[58] Field of Search ............................. 73/32 A, 32 R

[56] References Cited

U.S. PATENT DOCUMENTS 3,706,220  12/1972  Miller .................................. 73/32 A
3,769,831  11/1973  Schiatter ............................. 73/32 R Primary Examiner—Jerry W. Myracle
Attorney, Agent, or Firm—A. Donald Stolzy

[57] ABSTRACT

A plug for a vibration densitometer probe to obviate calibration shifts caused for a number of reasons.

8 Claims, 19 Drawing Figures

DENSITOMETER

BACKGROUND OF THE INVENTION

This invention relates to vibration densitometers, and more particularly, to an improved densitometer having modest or very little calibration shift.

A calibration shift can occur between gases, in a combination of gases, because of a drop in driving voltage, because of a phase shift, and for other reasons.

SUMMARY OF THE INVENTION

In accordance with the present invention, the above-described and other disadvantages of the prior art are overcome by providing a vibration densitometer probe plug.

The above-described and other advantages of the present invention will be better understood from the following detailed description when considered in connection with the accompanying drawings.

BRIEF DESCRIPTION OF THE DRAWINGS

In the drawings, which are to be regarded as merely illustrative.

DESCRIPTION OF THE PREFERRED EMBODIMENTS

Figure 1:
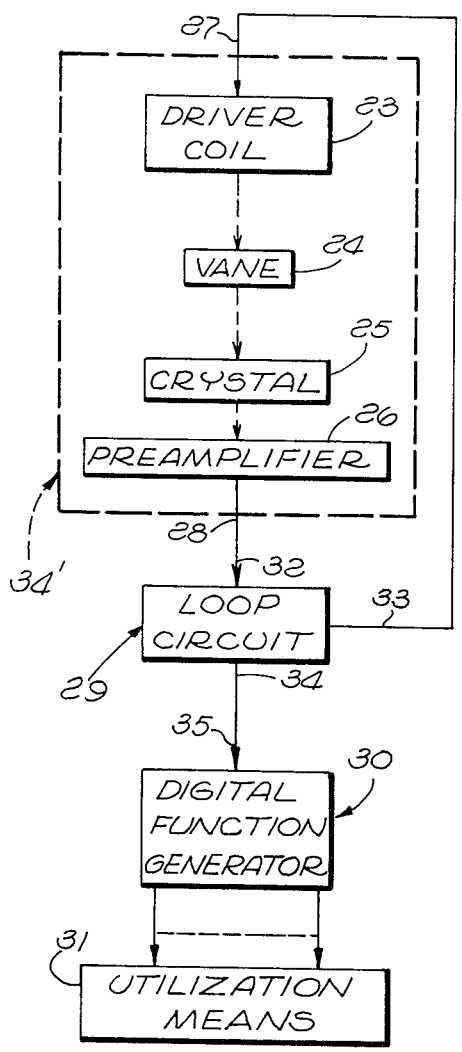
FIG. 1 is a block diagram of a densitometer constructed in accordance with the present invention.

In the drawings, in FIG. 1, a vibration densitometer probe is indicated at 34' having a driver coil 23, a vane 24, a piezoelectric crystal 25 and a preamplifier 26.

Probe 34' has an input lead 27 and an output lead 28.

Other blocks shown in FIG. 1 are a loop circuit 29, a digital function generator 30 and utilization means 31. Loop circuit 29 has an input lead 32 and output leads 33 and 34. Digital function generator 30 has an input lead 35 connected from loop circuit output lead 34. The output of digital function generator 30 is connected to utilization means 31.

The output lead 28 of probe 34' is connected to the input lead 32 of loop circuit 29. The input lead 27 of probe 34' is connected from the output lead 33 of loop circuit 29. Probe 34' and loop circuit 29 form a closed loop electromechanical oscillator. Vane 24 is submerged in a fluid. The density of the fluid is a function of the frequency at which vane 24 vibrates.

Digital function generator 30 may have its input lead 35 connected from lead 33 or at other points in loop circuit 29. Loop circuit 29 impresses a square wave voltage on input lead 35 of digital function generator 30 having a mark-to-space ratio of 1:1.

Utilization means 31 shown in FIG. 1 may be a density indicator, a specific gravity indicator, a process controller or otherwise.

Throughout this description, reference will be made to the text of certain U.S. patents. These patents are listed for convenience as follows:

U.S. Pat. No. 3,677,067
U.S. Pat. No. 3,706,220
U.S. Pat. No. 3,738,155
U.S. Pat. No. 3,741,000
U.S. Pat. No. 3,775,597
U.S. Pat. No. 3,776,024
U.S. Pat. No. 3,783,259
U.S. Pat. No.3,795,136
U.S. Pat. No. 3,805,361
U.S. Pat. No. 3,808,875
U.S. Pat. No. 3,823,310
U.S. Pat. No. 3,832,884
U.S. Pat. No. 3,842,655
U.S. Pat. No. 3,952,592

Figure 2:
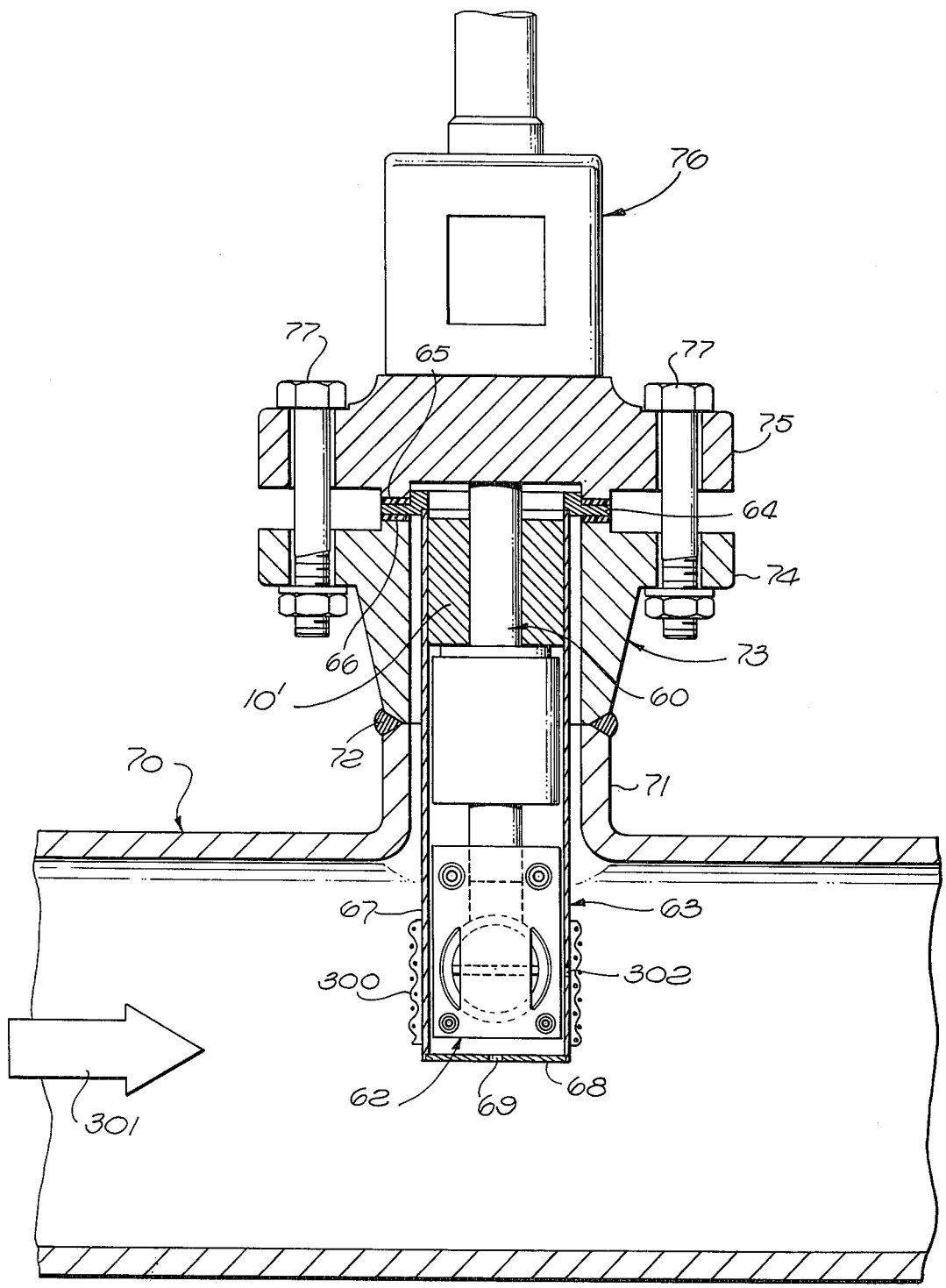
FIG. 2 is a vertical sectional view, partly in elevation, through a pipeline having a shielded densitometer probe mounted in a well therein in accordance with the present invention.
Figure 3:
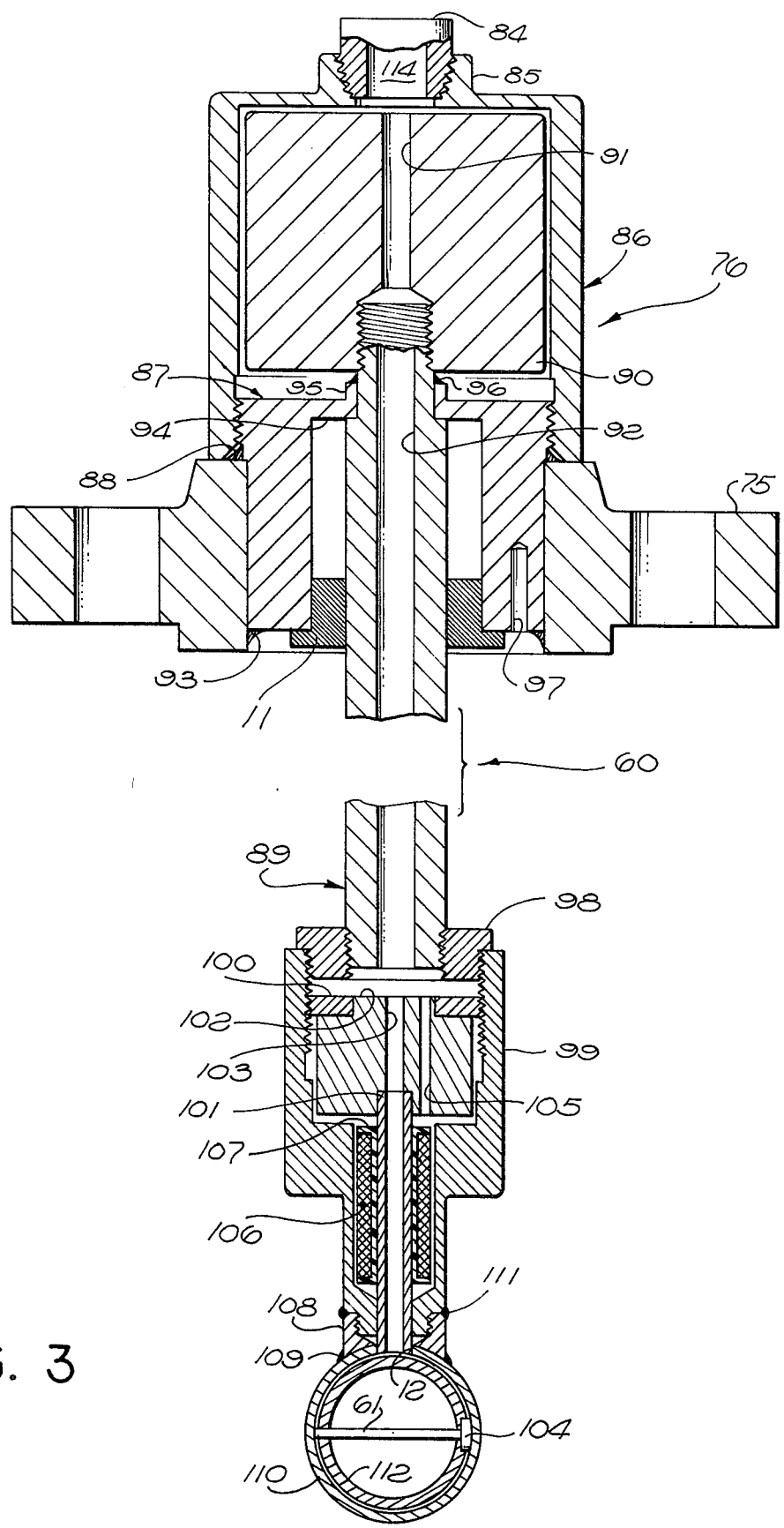
FIG. 3 is a vertical sectional view through a portion of the densitometer probe illustrated in FIG. 2.

Probe 34' shown in FIG. 1 may be conventional except for cylinder 10' in FIG. 2 or ferrule 11' in FIG. 3, both made of polytetrafluoroethylene or other material. Probe 34' may otherwise be similar to a probe shown in any of the above-listed patents.

Preamplifier 26 shown in FIG. 1 may be conventional. All of the structures shown in FIG. 1 may be identical to those shown in U.S. Pats. Nos. 3,878,374 and 3,958,446 except cylinder 10' shown in FIG. 2 and ferrule 11'shown in FIG. 3.

OPERATION

In the embodiment of the invention shown in FIG. 1, probe 34' and loop circuit 29 provide an electromechanical oscillator which oscillates at a frequency dependent upon the density of the fluid in which vane 24 is immersed. The same is true of the pulse repetition frequency of the square wave voltage applied to the input lead 35 of digital function generator 30.

Digital function generator 30 may be described as a digital linearization circuit. It produces a digital output directly proportional to density from the input signal thereto impressed upon the input lead 35 thereto.

In accordance with the foregoing, the word "densitometer" is hereby defined to include or not include utilization means 31. Note will be taken that the densitometer in many cases will be manufactured and sold without any utilization means 31. Such utilization means 31 would be supplied by the customer.

One embodiment of the present invention is illustrated in FIG. 2. A densitometer probe 60 is shown in FIG. 2 including a vane 61 and a shield 62 located in a well 63. Well 63 is formed of a ring 64 having annular gaskets 65 and 66 bonded on opposite sides thereof. A cylinder 67 then has an upper open end sealed to ring 64 and a disk 68 sealing the lower thereof except for a drain hole 69. A 50 to 100 micron mesh 300 of a cylindrical shape substantially completely surrounds cylinder 67 and may be brazed thereto at its upper and lower edges.

If fluid flow is in the direction of an arrow 301, a hole 302 forms a fluid exit hole.

A pipeline is illustrated at 70 having a hollow cylindrical projection 71 which is welded at 72 to a fitting 73 that has a flange 74 bolted to a flange 75 of an assembly 76 at preferably three or more or, for example, eight places 77.

Cylinder 10', fixed or not to well 63 and/or fixed or not to probe 60, prevents the calibration shift.

Figure 15:
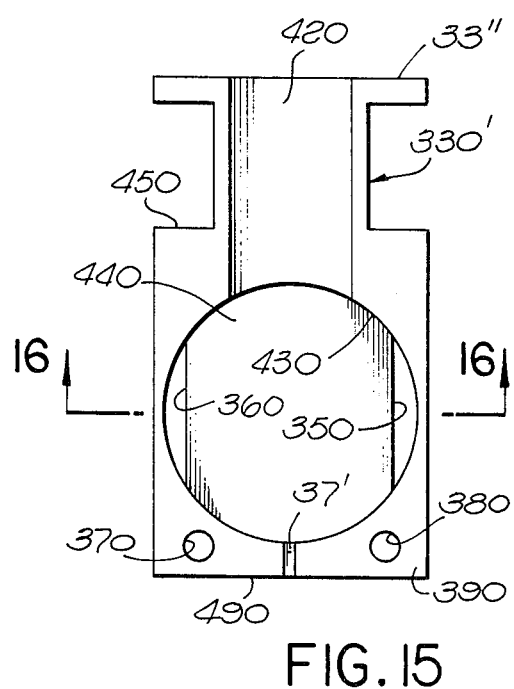

A vertical sectional view of probe 60 is shown in FIG. 15 except that ferrule 11' is added and fixed to body 87 and cylinder 10' has been omitted. Assembly 76 includes a nipple 84 threaded into a hollow cylindrical projection 85 of an end cap 86. End cap 86 is threaded to a body 87. Flange 75, end cap 86 and body 87 are welded or soldered together at 88. A hollow shaft 89 is externally threaded into a cylinder 90 that is solid except for a hole 91 which extends completely therethrough and is in communication with the hollow interior 92 of shaft 89. Body 87 is welded at 93 to flange 75, and is provided with a thin web 94 which has an upwardly extending cylindrical projection 95 that is welded at 96 to shaft 89 and to cylinder 90. Body 87 may be provided with a pin hole 97, if desired, so that it may be held while end cap 86 is turned or threaded thereto.

Shaft 89 is, in turn, fixed to a ferrule 98 by being threaded thereinto. Ferrule 98, in turn, is fixed to a body 99 by being threaded thereinto.

A ring 100 is threaded into body 99. A magnetostrictive tube 101 which is hollow and open at both ends is press fit into a body 102. Body 102 may have one hole 103 to receive conventional lead wires (not shown) from a piezoelectric crystal 104, and a hole 105 to receive lead wires from a drive coil 106 wound on a dielectric spool 107 press fit onto tube 101. A ferrule 108 is welded at 109 to a cylinder 110. Body 99 is threaded into ferrule 108 and welded thereto at 111. Tube 101 extends, at the bottom thereof, through a circular hole 12 in cylinder 110 and bears against the external cylindrical surface of a cylinder 112. Vane 61 is fixed inside cylinder 110 in a manner identical to that illustrated in the said U.S. Pat. No. 3,677,067. The same is true of crystal 104.

The utility of a vibration densitometer employing the structure disclosed herein is described in detail in the last-mentioned patent. The embodiments of the invention illustrated in FIGS. 2 and 3 have additional utility in that through their use erroneous readings are avoided over large density and flow rate ranges.

Cylinders 110 and 112, vane 61 and crystal 104 may be identical to those disclosed in the last mentioned patent, if desired. Tube 101 is slidable through the lower end of body 99 and is slidable through the said circular hole through cylinder 110, as is known from the said last mentioned patent.

A more detailed explanation of the operation of a vibration densitometer employing the structure disclosed herein is set forth in the said last mentioned patent.

It is common to use a preamplifier in the probe. Such a preamplifier may be employed at 114 in FIG. 3, or at any other convenient location, as desired.

Ferrule 11 in FIG. 3 also prevents calibration shift.

Figure 4:
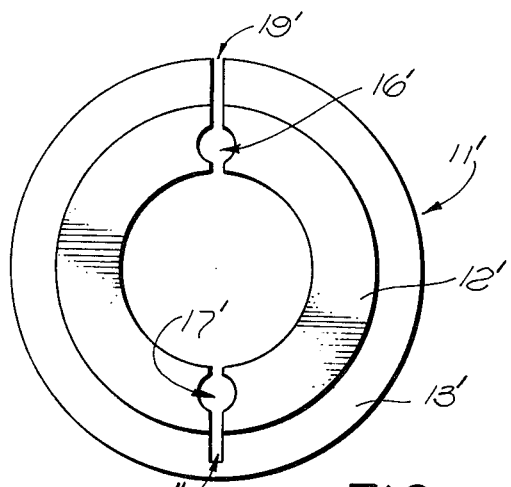
FIG. 4 is a top plan view of a part shown in FIG. 3.
Figure 5:
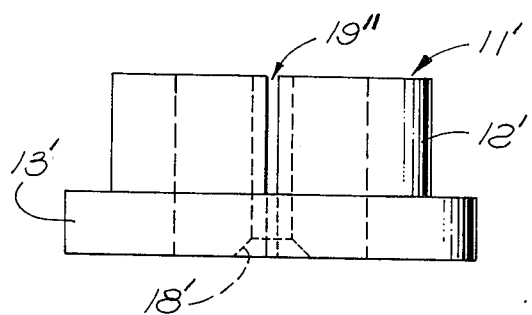
FIG. 5 is a side elevational view of the part shown in FIGS. 3 and 4.
Figure 6:
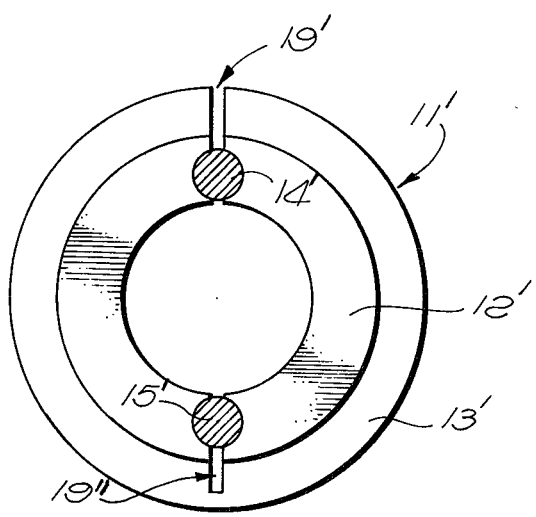
FIG. 6 is a top plan view of the part shown in FIGS. 3 and 4, but with mounting screws attached.

As shown in FIGS. 4, 5 and 6, ferrule 11' is cylindrical at 12' with a flange 13'. Tapered screws 14' and 15' are threaded into respective holes 16' and 17'. Holes 16' and 17' are countersunk at 18'. Slots are shown at 19' and 19''.

Figure 7:
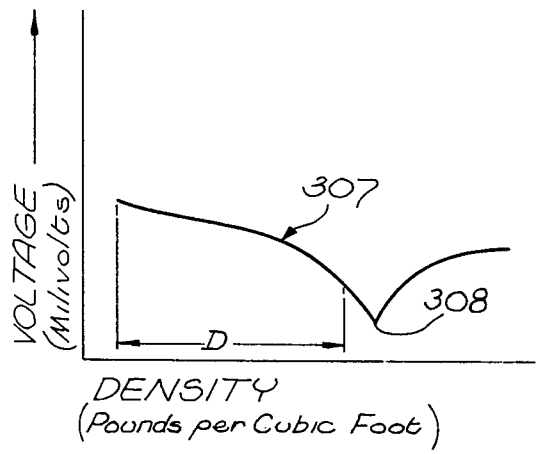
FIGS. 7, 8, 9 and 10 are graphs of a group of waveforms characteristic of the operation of the instrument of the present invention.

Not infrequently, the crystal output voltage versus density curve appears as indicated at 307 in FIG. 7. Unfortunately, without cylinder 10' or ferrule 11' the curve has a notch at 308, has a phase shift thereat, and has an inaccurate calibration shift thereat. This makes the usable span equal to D. Thus, it is an outstanding feature of the present invention that when either cylinder 10' or ferrule 11' is employed, the curve 307 can be converted to the curve 307' shown in FIGS. 7 and 8 without the notch 308, and the usable span thereof is increased to the extent indicated by E in FIG. 8.

Figure 8:
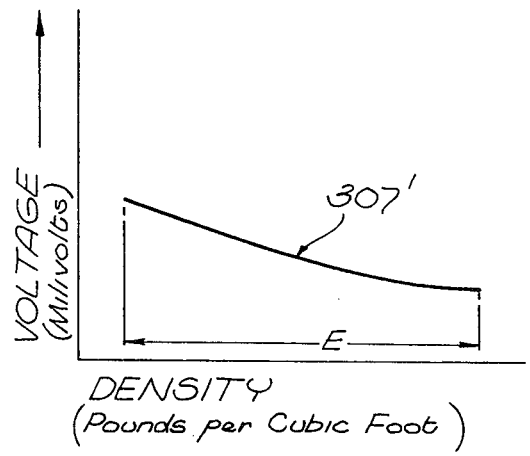
Figure 9:
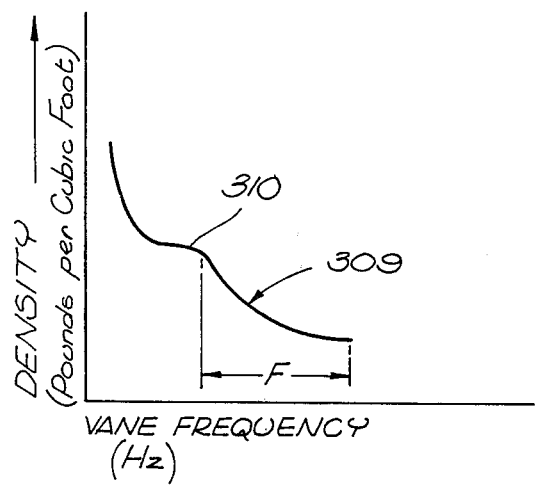
Figure 10:
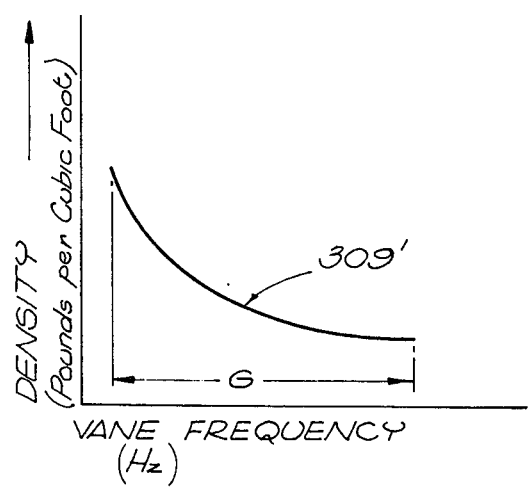

As in a fashion similar to that described in connection with FIGS. 7 and 8, in FIG. 9, the density versus vane vibrational frequency curve 309 is illustrated with a discontinuity 310. Because of the discontinuity 310, the instrument has a usable range of F. Again, it is an outstanding feature of the present invention that by employing cylinder 10' or ferrule 11', the usable span F of curve 309' is increased because the curve 309 is converted to the curve 309' shown in FIG. 10 having the substantially larger usable span G.

The word "fluid" is hereby defined to mean liquid and/or gas depending upon in which medium the instrument is operative.

Figure 11:
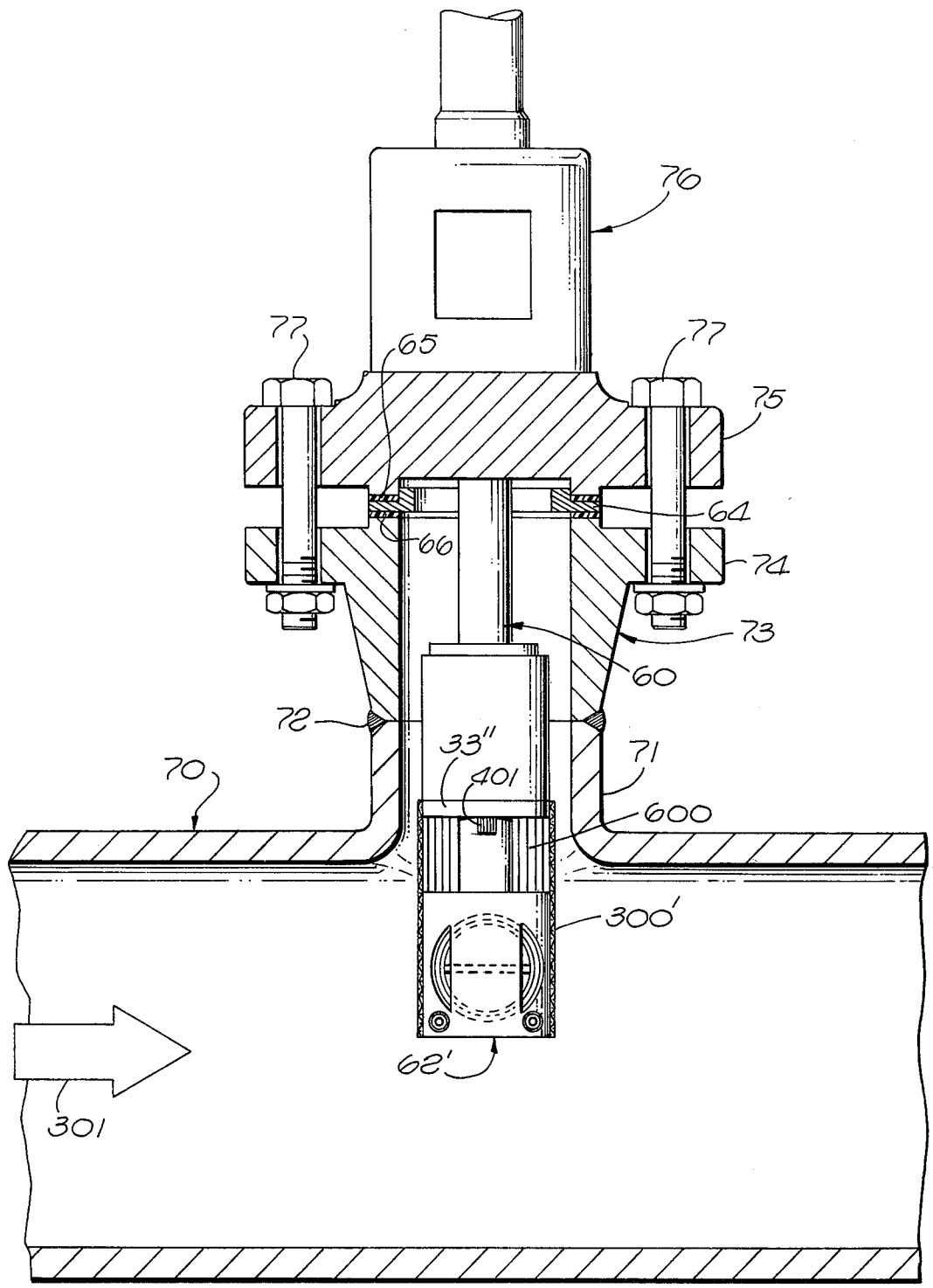
FIG. 11 is an elevational view, partly in section, of another embodiment of the present invention.
Figure 17:
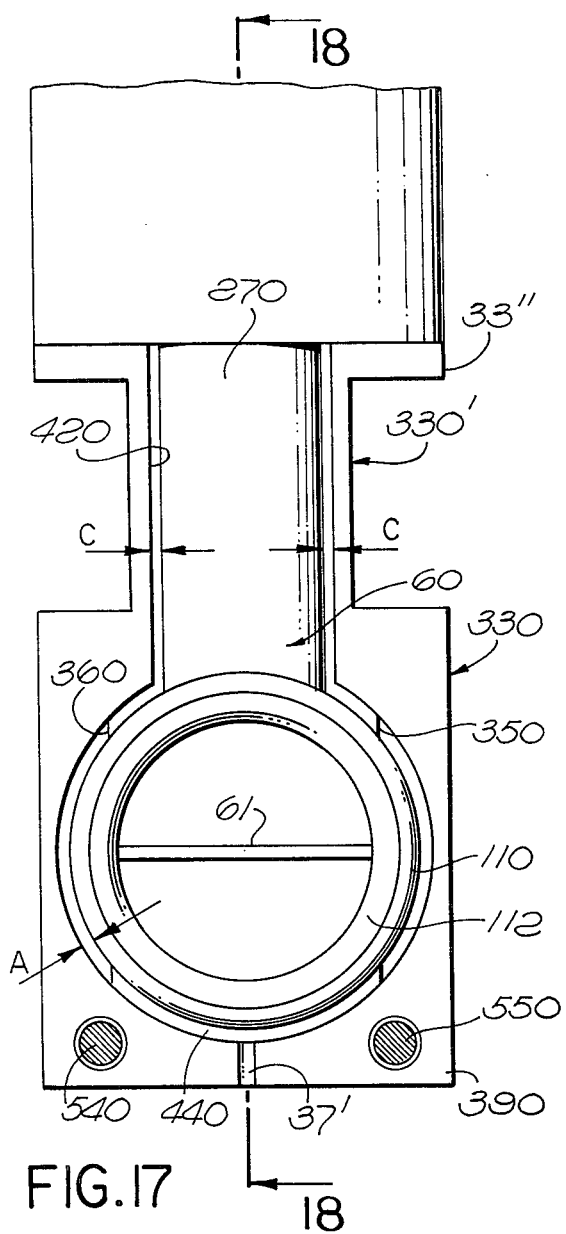
FIGS. 17 and 18 are elevational and vertical sectional views of the shield mounted on the probe.

Probe 60 vane 61 are shown in FIG. 11 and 17.

The probe 60 may be identical to the probe shown in the said U.S. Pat. No. 3,741,000 with certain exceptions. All these exceptions are noted hereinafter.

The said U.S. Pat. No. 3,741,000 is referred to hereinafter as the "later" patent.

In accordance with the present invention, the probe 60 may have a shield 62' shown in FIG. 11 mounted thereon such that the shield does not touch shank 270 (FIGS. 17 and 18) or any structure of probe 60 at a location therebelow. Both halves of the shield are substantially identical. One-half of the shield is indicated at 330 in FIG. 12. Shield half 330 has a generally cylindrical external surface at 340. However, this cylindrical surface is interrupted by vertical slots 350 and 360. Holes 370 and 380 extend perpendicularly completely through shield half 330. Holes 370 and 380 have axes which are normal to a flat surface 390.

Both of the holes 370 and 380 serve the same purpose. An Allen head screw is positioned in each of the holes 370 and 380 to hold the two shield halves together at its lower end. The screws for the holes 370 and 380 cause surface 390 to abut the corresponding surface of the other shield half.

Shield half 330 has a vertical half bore 420, the full bore of which may have a diameter of 0.78 inch for an outside diameter of 0.75 inch of shank 270 shown in FIG. 2. The shield is mounted so that the external cylindrical surface of shank 270 extends through the full bore concentric therewith. See FIG. 14. Shield half 330 has an extension 330'' with a flange 33'' (FIGS. 11 to 18) for cap screw mounting to the driver assembly via holes 33''' through flanges 33'''.

Figure 12:
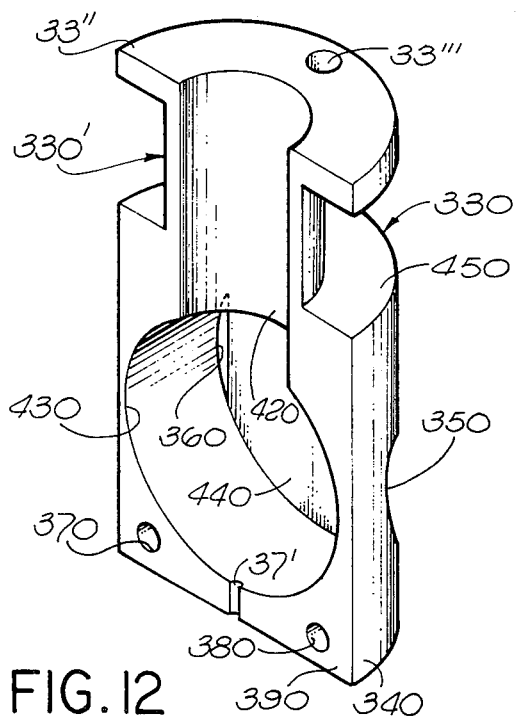
FIGS. 12 and 13 are orthogonal views of a portion of the shield shown in FIG. 11.

Shield half 330, in FIG. 12, has another partial cylindrical bore 430, the axis of which is normal to the axis of the bore 420. Bore 430 terminates in a flat surface 440 which is generally circular except for the slots 350 and 360. Surface 440 is parallel to surface 390. Hole 37' is a drain hole.

In manufacture, the openings 350 and 360 are conveniently provided at the same time that bore 430 is provided in that the bore 430 is extended to an extent such that the boring tool interrupts the external surface 340 of shield half 330 and thereby provides the apertures 350 and 360. However, boring is stopped short of going completely through the shield half 330 leaving material, one surface of which is illustrated 440.

Figure 13:
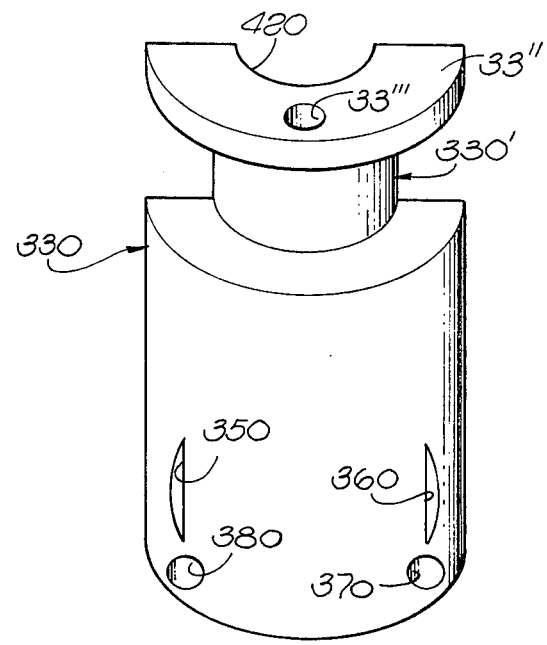

Shield half 330 is again shown in FIG. 13. Note will be taken in both of the FIGS. 12 and 13 that shield half 330 has an upper flat surface 450 which is generally semi-circular and lies in a plane perpendicular to the axis of bore 420.

Figure 14:
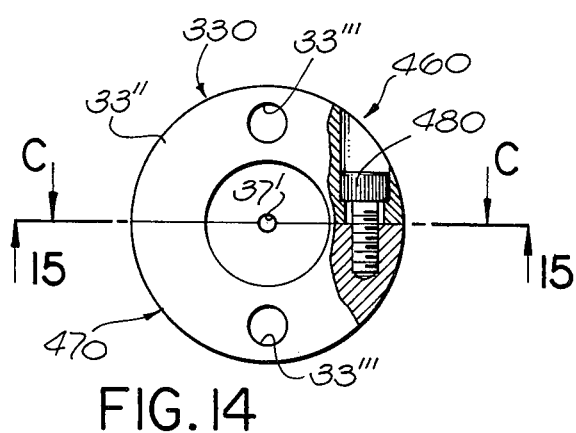
FIGS. 14, 15 and 16 are broken away top plan, vertical elevation, and transverse sectional views of the shield.

The entire shield is illustrated at 460 in FIG. 14. Shield half 330 is shown in FIG. 14 with the other shield half 470. A typical Allen head screw 480 is shown in FIG. 14. Both of the screws may be identical.

Shield half 330 is again shown in FIG. 15. Note that the upper and lower surfaces 450 and 490, respectively, of sheild half 330 in FIG. 15 are flat and parallel. Surface 490 has the exact shape of one-half of a circle.

Figure 16:
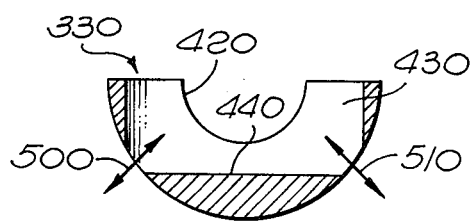

Shield half 330 is again shown in FIG. 16 having openings allowing ingress and egress of fluid in the direction of arrows 500 and 510.

In FIG. 17, screws are shown at 540 and 550. The view of FIG. 17 is quite similar to the view of FIG. 15 with shield 460 clamped onto the probe driver assembly. Shield half 330 is shown in FIG. 17

In FIG. 17, note will be taken that a cylinder 112 is fixed inside cylinder 110 (FIGS. 3, 11 and 17). This construction is described in the said U.S. Pat. No. 3,677,067. Cylinders 110 and 112 are substantially the same length and are substantially flush at each of their opposite ends. They are somewhat rounded at each of their opposite ends.

In FIG. 17, note will be taken that cylinder 110 is everywhere a distance A from bore 430. However, shield halves 330 and 470 are mounted upon the probe driver assembly with cap screws 401 as shown in both FIGS. 17 and 18.

In FIG. 18, probe 60 is shown again with shield halves 330 and 470 mounted on the driver assembly. Shield half 470 has one of its two openings indicated at 560'.

Figure 18:
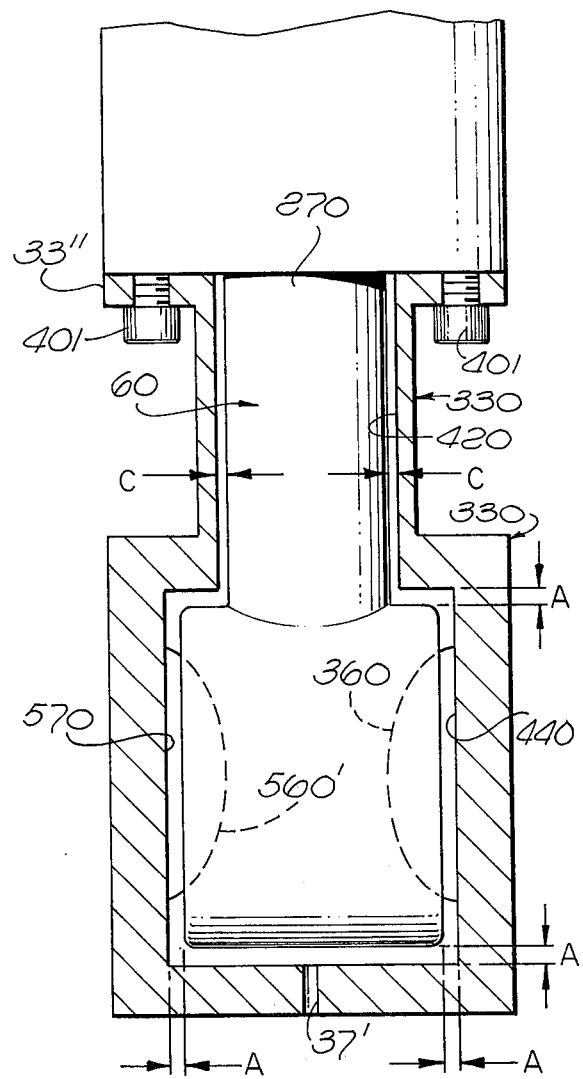

In FIG. 18, it will be noted that except for the three openings 350, 360 and 560', and the fourth symmetrical one, not shown, shield 460 encases an assembly which includes cylinder 110 and 61. The same is not fluid tight except for openings 350, etc., but it may be fluid tight, and it allows very little fluid flow into or out of the shield 460 for the openings 350, etc.

Again, in FIG. 18, note will be taken that cylinder 110 is spaced from surface 440, a corresponding surface 570 of shield half 470, and completely around the external surface of cylinder 110 as shown in both 17 and 18, and as shown at A in both FIGS. 17 and 18. Shank 270 is similarly spaced from shield half 460 as shown at C in FIGS. 17 and 18.

Although probe 60 may or may be made of heavier materials such as as stainless steel, shank 270, cylinder 110 and cylinder 112 may be made of stainless steel. Vane 61 may be made of Ni-Span-C or another relatively temperature insensitive material. Shield half 460 need not necessarily be made of a lighter material and need not necessarily be made of aluminum, but is preferably made of aluminum.

A section taken on the line C—C in FIG. 14 would look approximately the same as FIG. 15.

Figure 19:
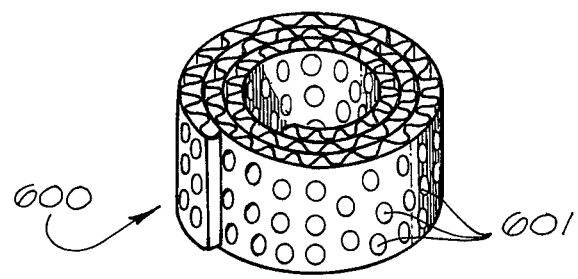
FIG. 19 is a perspective view of a porous body which improves accuracy over a wide range while having no well flow or heat exchange restriction to the probe vane.

In FIG. 11, the well has been removed and the spiral corrugated paper board 600 with holes 601 added. See FIG. 19. In FIG. 11, wire mesh is attached to the shield 62'. Shield 62' may be identical to shield 460 in FIG. 14.

For a further explanation of the structures disclosed herein, see U.S. Pat. No. 3,878,374 issued Apr. 15, 1975.

What is claimed is:

1. A vibration densitometer comprising: an electromechanical oscillator including a probe having input and output leads, a lower end, and a loop circuit having an input lead connected from said probe output lead, and an output lead connected from said probe input lead; a shield fixed to said probe lower end, said probe having a vane supported at said probe lower end; driver means to vibrate said vane, said driver means being located above said vane, an upper mounting; an extension fixed to said upper mounting and attached to said driver means, said shield defining an annular recess; and a perforate annular body positioned around said shield in said recess thereof.

2. The invention as defined in claim 1, wherein a function generator is connected from said loop circuit to produce an output directly proportional to the density of the fluid in which said vane is immersed, and utilization means connected from said function generator.

3. The invention as defined in claim 2, wherein said perforate annular body includes an approximately right hollow cylinder formed by rolling perforate corrugated board into a spiral.

4. The invention as defined in claim 2, including a wire mesh fixed around and to said shield, said perforate annular body being located in an annular space defined by parallel annular surfaces of said shield normal to the length of said extension, a cylindrical shield portion concentric to said extension, and said wire mesh.

5. The invention as defined in claim 1 wherein said perforate annular body includes an approximately right hollow cylinder formed by rolling perforate corrugated board into a spiral.

6. The invention as defined in claim 5, including a wire mesh fixed around and to said shield, said said perforate annular body being located in an annular space defined by parallel annular surfaces of said shield normal to the length of said extension, a cylindrical shield portion concentric to said extension, and said wire mesh.

7. The invention as defined in claim 1, including a wire mesh fixed around and to said shield, said perforate annular body being located in an annular space defined by parallel annular surfaces of said shield normal to the length of said extension, a cylindrical shield protion concentric to said extension, and said wire mesh.

8. The invention as defined in claim 7, wherein said perforate annular body includes an approximately right hollow cylinder formed by rolling perforate corrugated board into a spiral.

* * * * *